United States Patent
Jiang et al.

(10) Patent No.: US 11,969,572 B2
(45) Date of Patent: Apr. 30, 2024

(54) DISINFECTION CAP

(71) Applicant: Becton, Dickinson and Company, Franklin Lakes, NJ (US)

(72) Inventors: Chang Jiang, Butler, NJ (US); Amir Harandi, Bloomingdale, NJ (US); Jiayu Liu, Bloomingdale, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 17/229,157

(22) Filed: Apr. 13, 2021

(65) Prior Publication Data

US 2021/0322751 A1    Oct. 21, 2021

Related U.S. Application Data

(60) Provisional application No. 63/011,356, filed on Apr. 17, 2020.

(51) Int. Cl.
*A61M 39/20*    (2006.01)

(52) U.S. Cl.
CPC .......... *A61M 39/20* (2013.01); *A61M 2207/00* (2013.01)

(58) Field of Classification Search
CPC .......... A61M 2205/0205; A61M 39/20; A61M 39/162; A61M 2207/00; A61M 2039/1038
See application file for complete search history.

(56) References Cited

U.S. PATENT DOCUMENTS

| | | |
|---|---|---|
| 3,403,679 A | 10/1968 | Sinclair et al. |
| 4,597,758 A | 7/1986 | Aalto et al. |
| 4,642,102 A | 2/1987 | Ohmori |
| 4,711,363 A | 12/1987 | Marino |
| 4,738,376 A | 4/1988 | Markus |
| 4,906,231 A | 3/1990 | Young |

(Continued)

FOREIGN PATENT DOCUMENTS

| | | |
|---|---|---|
| CA | 2523133 C | 2/2013 |
| CN | 1322119 A | 11/2001 |

(Continued)

OTHER PUBLICATIONS

"Non-Final Office Action in U.S. Appl. No. 17/076,102 dated Aug. 24, 2021, 10 pages".

(Continued)

*Primary Examiner* — Brandy S Lee
(74) *Attorney, Agent, or Firm* — Servilla Whitney LLC

(57) ABSTRACT

A disinfection cap is described for connection to a medical connector, the disinfection cap includes a housing having a top wall and sidewall forming a cavity, an open cell foam structure disposed within the cavity and a closed cell foam structure disposed against the open cell foam structure, the closed cell foam structure having an interference fit between the closed cell foam structure and the inner surface of the housing. The closed cell foam structure may have a polygonal or star shape, wherein fluid can flow through a gap formed between the closed cell foam structure and the inner surface of the cavity. The open cell foam structure may be impregnated with disinfectant, whereby compression of the open cell foam structure causes excretion of the disinfectant upon insertion of a luer connector.

21 Claims, 9 Drawing Sheets

(56) References Cited

U.S. PATENT DOCUMENTS

| | | |
|---|---|---|
| 5,084,017 A | 1/1992 | Maffetone |
| 5,496,288 A | 3/1996 | Sweeney |
| 5,676,406 A | 10/1997 | Simmons et al. |
| 5,755,696 A | 5/1998 | Caizza |
| 5,984,123 A | 11/1999 | Mogami et al. |
| 6,565,529 B1 | 5/2003 | Kimber et al. |
| 6,632,199 B1 | 10/2003 | Tucker et al. |
| 7,083,605 B2 | 8/2006 | Miyahara |
| 8,012,131 B2 | 9/2011 | Moser et al. |
| 8,388,894 B2 | 3/2013 | Colantonio |
| 8,647,308 B2 | 2/2014 | Solomon et al. |
| 8,715,231 B2 | 5/2014 | Woehr |
| 8,721,627 B2 | 5/2014 | Alpert et al. |
| 8,777,504 B2 | 7/2014 | Shaw et al. |
| 8,961,475 B2 | 2/2015 | Solomon et al. |
| 9,039,989 B2 | 3/2015 | Lui et al. |
| 9,132,223 B1 | 9/2015 | Wakeel |
| 9,192,449 B2 | 11/2015 | Kerr et al. |
| 9,867,975 B2 | 1/2018 | Gardner et al. |
| 10,099,048 B2 | 10/2018 | Chiu et al. |
| 10,166,381 B2 | 1/2019 | Gardner et al. |
| 10,376,686 B2 | 8/2019 | Burkholz et al. |
| 10,589,080 B2 | 3/2020 | Hitchcock et al. |
| 10,603,481 B2 | 3/2020 | Avula et al. |
| 10,871,246 B2 | 12/2020 | Marici et al. |
| 11,353,147 B2 | 6/2022 | Marici |
| 11,511,100 B2 | 11/2022 | Ryan |
| 11,628,288 B1 | 4/2023 | Solomon et al. |
| 2003/0093009 A1 | 5/2003 | Newby et al. |
| 2003/0209681 A1 | 11/2003 | Leinsing et al. |
| 2004/0039341 A1 | 2/2004 | Ranalletta |
| 2004/0044318 A1 | 3/2004 | Fiser et al. |
| 2005/0147525 A1 | 7/2005 | Bousquet |
| 2005/0197646 A1 | 9/2005 | Connell et al. |
| 2007/0060904 A1 | 3/2007 | Vedrine et al. |
| 2008/0010766 A1 | 1/2008 | Kaufman et al. |
| 2008/0171995 A1 | 7/2008 | Vitullo et al. |
| 2008/0177250 A1 | 7/2008 | Howlett et al. |
| 2010/0000040 A1 | 1/2010 | Shaw et al. |
| 2010/0049170 A1 | 2/2010 | Solomon et al. |
| 2010/0050351 A1 | 3/2010 | Colantonio et al. |
| 2010/0100056 A1 | 4/2010 | Cawthon et al. |
| 2011/0046603 A1 | 2/2011 | Felsovalyi et al. |
| 2011/0054440 A1 | 3/2011 | Lewis |
| 2011/0213341 A1 | 9/2011 | Solomon et al. |
| 2011/0264037 A1 | 10/2011 | Foshee et al. |
| 2012/0039764 A1 | 2/2012 | Solomon et al. |
| 2012/0111368 A1 | 5/2012 | Rahimy et al. |
| 2012/0123386 A1 | 5/2012 | Tsals |
| 2012/0302997 A1 | 11/2012 | Gardner et al. |
| 2013/0085474 A1 | 4/2013 | Charles et al. |
| 2013/0171030 A1* | 7/2013 | Ferlic ............... A61M 39/20 422/294 |
| 2013/0197485 A1* | 8/2013 | Gardner ............ A61M 39/162 604/533 |
| 2013/0338644 A1* | 12/2013 | Solomon ........... A61M 39/162 604/535 |
| 2014/0052074 A1 | 2/2014 | Tekeste |
| 2014/0150832 A1 | 6/2014 | Rogers et al. |
| 2015/0094666 A1 | 4/2015 | Bates et al. |
| 2016/0045629 A1 | 2/2016 | Gardner et al. |
| 2016/0067422 A1 | 3/2016 | Davis et al. |
| 2016/0158520 A1 | 6/2016 | Ma et al. |
| 2017/0203087 A1 | 7/2017 | Ryan et al. |
| 2018/0085568 A1 | 3/2018 | Drmanovic |
| 2018/0200145 A1 | 7/2018 | Sanders et al. |
| 2018/0200500 A1 | 7/2018 | Ziebol et al. |
| 2018/0237190 A1 | 8/2018 | Iwasaki |
| 2018/0243547 A1 | 8/2018 | Fox et al. |
| 2018/0256879 A1 | 9/2018 | Chiu et al. |
| 2018/0256883 A1 | 9/2018 | Follman et al. |
| 2019/0111245 A1 | 4/2019 | Gardner et al. |
| 2019/0151643 A1 | 5/2019 | Alpert |
| 2019/0234540 A1 | 8/2019 | Marici et al. |
| 2019/0308006 A1 | 10/2019 | Erekovcanski et al. |
| 2019/0351212 A1 | 11/2019 | Dudar et al. |
| 2020/0238070 A1 | 7/2020 | Ryan |
| 2021/0100996 A1 | 4/2021 | Wijesuriya et al. |
| 2021/0187267 A1 | 6/2021 | Jiang |
| 2022/0273931 A1 | 9/2022 | Jiang et al. |
| 2023/0080687 A1 | 3/2023 | Ryan |

FOREIGN PATENT DOCUMENTS

| | | |
|---|---|---|
| CN | 101631585 A | 1/2010 |
| CN | 101980746 A | 2/2011 |
| CN | 201807018 U | 4/2011 |
| CN | 102188766 A | 9/2011 |
| CN | 102448502 A | 5/2012 |
| CN | 103025374 A | 4/2013 |
| CN | 103083767 A | 5/2013 |
| CN | 204161736 U | 2/2015 |
| CN | 206198472 U | 5/2017 |
| DE | 20017013 U1 | 12/2000 |
| DE | 10247963 A1 | 5/2004 |
| DE | 202005004079 U1 | 7/2006 |
| EP | 0589379 A1 | 3/1994 |
| EP | 2832391 A1 | 2/2015 |
| EP | 3275490 A1 | 1/2018 |
| GB | 2408259 A | 5/2005 |
| GB | 2518646 A | 4/2015 |
| JP | H03139363 A | 6/1991 |
| JP | H04501672 A | 3/1992 |
| JP | 2001502191 A | 2/2001 |
| JP | 2001521792 A | 11/2001 |
| JP | 2004208740 A | 7/2004 |
| JP | 2008532701 A | 8/2008 |
| JP | 2008239164 A | 10/2008 |
| JP | 2010527276 A | 8/2010 |
| JP | 2012522593 A | 9/2012 |
| JP | 2015517377 A | 6/2015 |
| JP | 2016511119 A | 4/2016 |
| JP | 2016104214 A | 6/2016 |
| WO | 0019878 | 4/2000 |
| WO | 200024442 A1 | 5/2000 |
| WO | 200224551 A1 | 3/2002 |
| WO | 2011066586 A1 | 6/2011 |
| WO | 2013046857 A1 | 4/2013 |
| WO | 2014159346 A1 | 10/2014 |
| WO | 2015127285 A1 | 8/2015 |
| WO | 2015174953 A1 | 11/2015 |
| WO | 2016158144 A1 | 10/2016 |
| WO | 2017087400 A1 | 5/2017 |
| WO | 2017095373 A1 | 6/2017 |
| WO | 2018106508 A1 | 6/2018 |
| WO | 2018237090 A1 | 12/2018 |
| WO | 2019147906 A1 | 8/2019 |
| WO | 2019212637 A1 | 11/2019 |
| WO | 2020112767 A1 | 6/2020 |

OTHER PUBLICATIONS

Non-Final Office Action in U.S. Appl. No. 16/774,853 dated Feb. 1, 2022, 12 pages.

"PCT International Search Report and Written Opinion in PCT/US2021/027219 dated Oct. 22, 2021, 22 pages".

PCT International Search Report and Written Opinion in PCT/US2021/027214 dated Jul. 19, 2021, 14 pages.

PCT International Search Report and Written Opinion in PCT/US2021/027218 dated Jul. 22, 2021, 14 pages.

PCT International Search Report and Written Opinion in PCT/US2021/027220 dated Jul. 21, 2021, 15 pages.

PCT Invitation to Pay Additional Fees in PCT/US2021/027219, mailed on Jul. 22, 2021, 15 pages.

PCT Invitation to Pay Additional Fees in PCT/US2021/019546, mailed on Jun. 15, 2021, 17 pages.

* cited by examiner

DISINFECTION CAP

CROSS-REFERENCE TO RELATED APPLICATIONS

This application claims priority to U.S. Provisional Application No. 63/011,356, filed Apr. 17, 2020, the entire disclosure of which is hereby incorporated by reference herein.

TECHNICAL FIELD

The present disclosure relates to disinfection cap devices for disinfecting corresponding medical connectors. The present disclosure generally relates to a device for disinfecting and sterilizing access ports of medical connectors having a fitting. Generally, exemplary embodiments of the present disclosure relate to the fields of threaded or interlocking fittings, including medical caps and medical disinfection caps, and in particular caps and/or disinfection caps for uses with threaded fluid connectors. One or more exemplary embodiments of the present disclosure relate to male disinfection cap devices for disinfecting male threaded luer connectors.

BACKGROUND

Vascular access devices (VAD's) are commonly used therapeutic devices and include intravenous (IV) catheters. There are two general classifications of VAD's: peripheral catheters and central venous catheters. Bacteria and other microorganisms may gain entry into a patient's vascular system from access hub, port, or valve upon connection to the VAD to deliver the fluid or pharmaceutical. Each access hub, port, valve or connection is associated with some risk of transmitting a catheter related bloodstream infection (CRBSI), which can be costly and potentially lethal. In order to decrease CRBSI cases and to ensure VAD's are used and maintained correctly, standards of practice have been developed, which include disinfecting and cleaning procedures. Disinfection caps have been added to the Society for Healthcare Epidemiology of America (SHEA) guidelines and the Infusion Nurses Standards (INS) guidelines.

In developed markets, when utilizing an IV catheter, a needleless connector will typically be used to close off the system and then subsequently accessed to administer medication or other necessary fluids via the catheter to the patient. INS Standards of Practice recommend the use of a needleless connector and state that it should be "consistently and thoroughly disinfected using alcohol, tincture of iodine or chlorhexidine gluconate/alcohol combination prior to each access." The disinfection of the needleless connector is ultimately intended to aid in the reduction of bacteria that could be living on the surface and possibly lead to a variety of catheter related complications including CRBSI. Nurses will typically utilize a 70% isopropyl alcohol (IPA) pad to complete this disinfection task by doing what is known as "scrubbing the hub." However, compliance to this practice is typically very low. In addition to a lack of compliance to "scrubbing the hub", it has also been noted through clinician interviews that there is often a variation in scrub time, dry time and the number of times the needleless connector is scrubbed.

The need to protect female and male luer connectors to reduce central line-associated bloodstream infections (CLABSI) and peripheral line-associated bloodstream infection (PLABSI) has been rising. Intravenous gravity sets and threaded male luer connections on syringes are subject to contamination when not protected properly. Currently when IV connectors are disconnected from central lines or peripheral lines to temporarily discontinue infusion, nurses often loop the male luer connector to a Y-site needle-free connector or wrap the male luer connector in a piece of Isopropyl Alcohol ("IPA") impregnated wipe or cloth. However, such protection is very weak and does not protect the luer from touch contamination properly. Male disinfection caps have become the state of art disinfection and protection device to disinfect and create a physical barrier on male luer connector to prevent microbial growth.

Throughout the sequence of procedures associated with the transmission of a microorganism that can cause a CRBSI, there are many risks of contact or contamination. By way of example, contamination can occur during drug mixing, attachment of a cannula, and insertion into the access hub. Furthermore, threaded male luer connectors have an open luer with an exposed lumen. Because the procedure to connect to a VAD is so common and simple, the risk associated with entry into a patient's vascular system has often been overlooked. Presently, the risk to hospitals and patients is a substantial function of the diligence of the clinician performing the connection, and this diligence is largely uncontrollable.

Disinfectants typically have a threshold limit for systemic exposure for infusion into blood stream due to biotoxicity of the disinfectants at high dosage. There is a need for a mechanism to prevent disinfectant from entering the lumen and fluid path while providing effective disinfection of the surrounding connector or fitting. Thus, there is a need for a disinfection device capable of blocking the lumen of open luers to facilitate the mitigation of such disinfectant ingress into connectors, thereby reducing risk of the disinfectant entering the blood stream.

SUMMARY

A first aspect of the present disclosure relates to a disinfection cap comprising a top wall, a cylindrical sidewall, an open bottom, an open cell foam structure, and a closed cell foam structure. The cylindrical sidewall has an inner surface defining a cavity. The open bottom is formed by the cylindrical sidewall with an opening to the cavity within said housing for receiving a hub of a luer connector. The open cell foam structure is disposed within the cavity, the open cell foam structure abutting a top wall of the cavity, the open cell foam structure being impregnated with disinfectant fluid in a pre-activated state. The closed cell foam structure is disposed against the open cell foam structure, the closed cell foam structure being configured as a blockage feature for fluidly blocking the hub of the luer connector. The hub of said luer connector is received within said inner surface of said cavity.

In one or more embodiments, the cavity extends essentially from an inner surface of said top wall toward said open bottom of said housing.

In one or more embodiments, the closed cell foam structure forms an interference fit between the closed cell foam structure and an inner surface of the housing. In one or more embodiments, the open cell foam structure is bonded to the closed cell foam structure. In one or more embodiments, insertion of the luer connector causes compression of the open cell foam structure, thereby releasing fluid.

In one or more embodiments, the closed cell foam structure has a polygonal shape.

In one or more embodiments, the closed cell foam structure has one of a multitude of corners which engage the inner surface of the housing in an interference fit.

In one or more embodiments, a gap is formed between one of a multitude of flat portions and the inner surface of the housing, the gap creating a pathway for disinfectant to flow through upon compression of the open cell foam structure.

In one or more embodiments, the closed cell foam structure has a hexagonal shape. In one or more embodiments, the closed cell foam structure has a pentagonal shape. In one or more embodiments, the closed cell foam structure has a star shape.

In one or more embodiments, he closed cell foam structure has one of a multitude of points which engage the inner surface of the housing in an interference fit. In one or more embodiments, a gap is formed between one of a multitude of inner points and the inner surface of the housing, the gap creating a pathway for disinfectant to flow through upon compression of the open cell foam structure.

In one or more embodiments, the closed cell foam structure has a four-point star shape. In one or more embodiments, the closed cell foam structure has a five point star shape.

In one or more embodiments, the disinfection cap further includes an at least one thread on said outer surface of the housing, said at least one thread being sufficient to interlock with a mating feature of the luer connector. In one or more embodiments.

In one or more embodiments, the hub is secured within said inner surface of said cavity by interlocking at least a portion of said at least one thread with a mating feature on said hub of said luer connector. In one or more embodiments, the inner surface of the cavity is secured by interference fit with the hub of the luer connector.

In one or more embodiments, a removable peelable seal covers an opening to the cavity.

In one or more embodiments, the open cell foam structure has a polygonal shape. In one or more embodiments, the open cell foam structure has a star shape.

A second aspect of the present disclosure relates to a method of manufacturing of a disinfection cap comprising bonding sheets of closed cell foam to open cell foam into a bonded open cell foam structure and closed cell foam structure, cutting the bonded open cell foam structure and closed cell foam structure into a shape and, inserting the bonded open cell foam structure and closed cell foam structure into a cavity of a housing of a disinfection cap.

In one or more embodiments, the method further comprises impregnating the open cell foam structure with disinfectant before inserting the bonded open cell foam structure and closed cell foam structure.

In one or more embodiments, the method further comprises impregnating the open cell foam structure with a disinfectant through a gap formed between a flat portion of the closed cell foam structure and an inner surface of the cavity of the housing.

In one or more embodiments, the method further comprises placing a peelable seal on an open end of the housing to seal the cavity and the disinfectant within.

DETAILED DESCRIPTION

Figure 1:
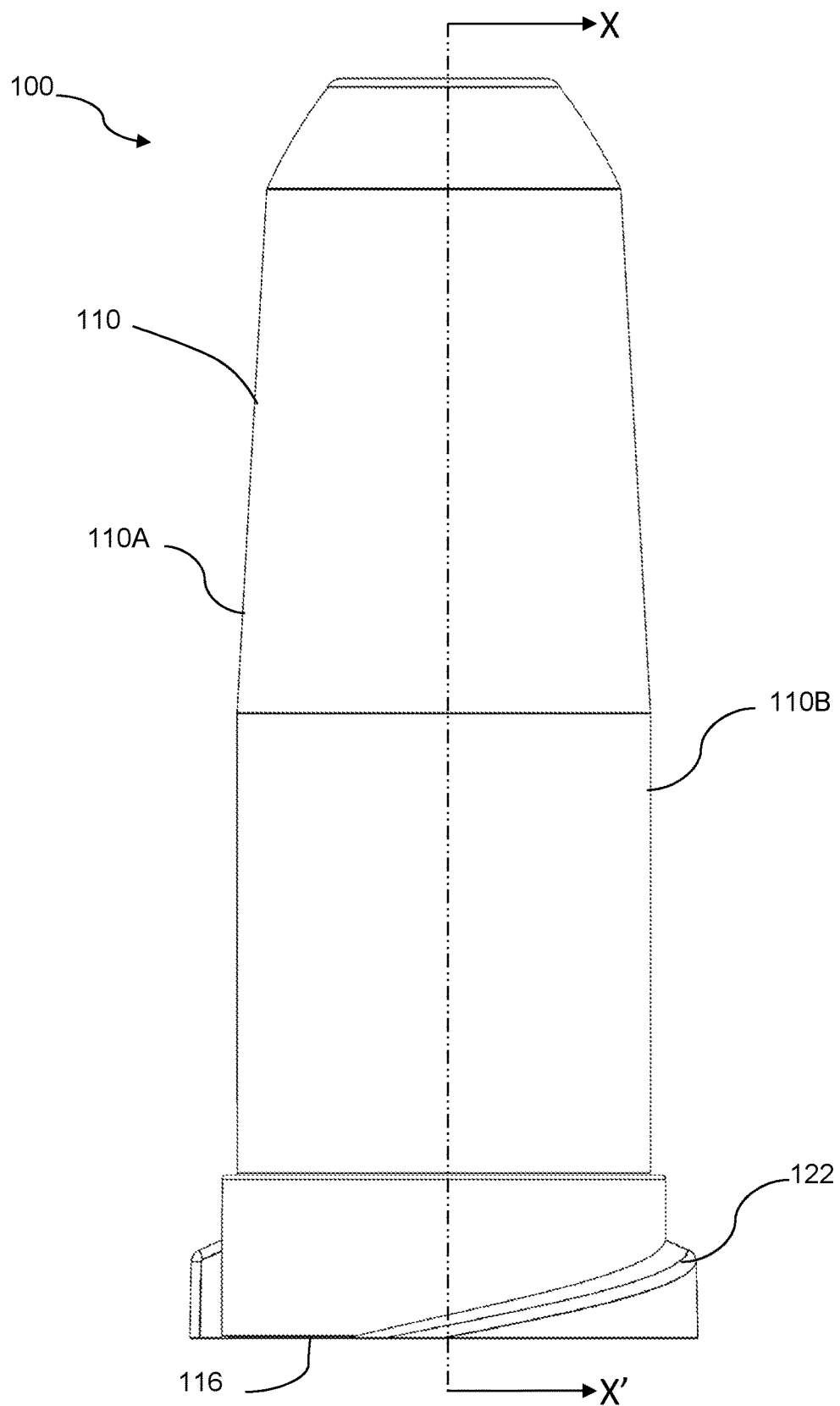
FIG. 1 illustrates a front view of a disinfection cap according to an exemplary first embodiment of the disclosure.

Embodiments of the disclosure pertain to a disinfection cap for connection to and disinfection of a medical connector, including threaded connections. In one or more embodiments, the medical connector is a luer connector or a needleless connector. In one or more embodiments, the medical connector is a male luer connector. In one or more embodiments, the medical connector is a female luer connector. The disclosure aims to provide a mechanism to prevent disinfectant from entering the fluid path of the medical connector while providing for effective disinfection for the hub and surrounding periphery of the medical connector.

Before describing several exemplary embodiments of the disclosure, it is to be understood that the disclosure is not limited to the details of construction or process steps set forth in the following description. The disclosure is capable of other embodiments and of being practiced or being carried out in various ways.

For purposes of the description hereinafter, the terms "upper", "lower", "right", "left", "vertical", "horizontal", "top", "bottom", "lateral", "longitudinal", and derivatives thereof shall relate to the disclosure as it is oriented in the drawing figures. However, it is to be understood that the disclosure may assume alternative variations and step sequences, except where expressly specified to the contrary. It is also to be understood that the specific devices and processes illustrated in the attached drawings, and described in the following specification, are simply exemplary embodiments of the disclosure. Hence, specific dimensions and other physical characteristics related to the embodiments disclosed herein are not to be considered as limiting.

As used herein, the use of "a," "an," and "the" includes the singular and plural.

As used herein, the term "catheter related bloodstream infection" or "CRBSI" refers to any infection resulting from the presence of a catheter or IV line.

As used herein, the term "Luer connector" refers to a connection collar that is the standard way of attaching syringes, catheters, hubbed needles, IV tubes, etc. to each other. The Luer connector consists of one or more interlocking tubes, slightly tapered to hold together with just a simple pressure/twist fit. Luer connectors can optionally include an additional outer rim of threading, allowing them to be more secure. The Luer connector is generally associated with a flush syringe and can interlock and connect to the end located on the vascular access device (VAD). A Luer connector comprises a distal end, a proximal end, an irregularly shaped outer wall, a profiled center passageway for fluid communication from the chamber of the barrel of a syringe to the hub of a VAD. A Luer connector also has a distal end channel that releasably attaches the Luer connector to the hub of a VAD, and a proximal end channel that releasably attaches the Luer connector to the barrel of a syringe. As used herein, the term "Luer connector" refers to a male luer connector or a female luer connector.

As used herein, the term "medical device" refers to common medical devices having threaded or interlocking connections, the connections having corresponding mating elements. By way of example but not limitation, a syringe may have a threaded connection which releasably interlocks with a secondary medical device such as a needleless connector of a catheter, an IV line and the like. The threaded connection may include a lumen defining a fluid path surrounded by a protruding wall having the threaded means for attaching to the secondary medical device.

As would be readily appreciated by skilled artisans in the relevant art, while descriptive terms such as "thread", "taper", "tab", "wall", "top", "side", "bottom" and others are used throughout this specification to facilitate understanding, it is not intended to limit any components that can be used in combinations or individually to implement various aspects of the embodiments of the present disclosure.

Embodiments of the disinfection cap of the present disclosure comprise a housing having a top wall defining a closed distal end, an open proximal end, and a substantially cylindrical sidewall extending from the closed end to the open proximal end, the sidewall having an inner surface. The cavity is configured for receiving a hub of a needleless connector. In one or more embodiments, the cavity is configured for receiving a hub a threaded needleless connector, having at least one thread on an exterior surface of the cylindrical sidewall that is sufficient to interlock with a mating feature of the threaded connection. Embodiments of the disinfection cap disclose the at least one thread of the disinfection cap engaging the mating feature of the threaded connection, and more specifically a luer connection. The cap further comprises an open cell foam structure functioning as an absorbent material configured to release a disinfectant fluid upon insertion of the hub of the needleless connector. Attached to the open cell foam structure is a closed cell foam structure which resists absorption of fluids. The closed cell foam structure is configured as a blockage feature to prevent disinfectant ingress into a fluid path of the hub of the luer connection. The open cell foam structure and closed cell foam structure are further configured to be immobilized within the cavity in a pre-activated state. In one or more embodiments, open proximal end includes a peripheral ledge extending radially outward from the outer surface of the sidewall defining an end face and an engagement surface for a peelable seal and/or septum for maintaining sterility of the cavity. The peelable seal reduces or prevents contamination of the cavity during shipping and storage of the disinfection cap. The peelable seal is generally kept sealed in the pre-activated state until just prior to an injection and/or aspiration procedure, at which time the peelable seal is removed. The removable seal minimizes entry of potential particulate hazard and also provides a substantially impermeable enclosure for the cavity prior to use of the disinfection cap. The removable seal provides a sufficient seal at a range of temperatures, pressures, and humidity levels.

The disinfection cap provides a mechanical barrier for connectors and contains a disinfectant fluid or an antimicrobial agent (hereinafter "fluid"). The disinfection cap of the present disclosure allows the practitioner to streamline the disinfecting process. The matters exemplified in this description are provided to assist in a comprehensive understanding of exemplary embodiments of the disclosure. Accordingly, those of ordinary skill in the art will recognize that various changes and modifications of the embodiments described herein can be made without departing from the scope and spirit of the disclosure. Also, descriptions of well-known functions and constructions are omitted for clarity and conciseness.

In particular, the practitioner may disinfect the needleless connector in a single motion by inserting or threading the disinfection cap onto the needleless connector of the medical device which causes the blockage feature to prevent fluid ingress into the fluid path of the hub and lumen of the needleless connector, while the insertion of the hub of the luer connector simultaneously causes the release of the fluid allowing for disinfection of the luer connector hub and its periphery due to compression of the open cell foam. In one or more embodiments, the disinfection cap may then be removed by removing or unthreading the disinfection cap from the luer connector. In one or more embodiments, the disinfection cap may remain connected to the luer connector until ready for use, providing for a disinfected, closed environment.

In an exemplary implementation of the embodiments of present disclosure, the disinfection cap includes integrated threads or tabs, and other features in any and all combinations allowing it to interface with a threaded fitting of a medical device. In preferred embodiments, the disinfection cap interfaces with a Luer fitting. Exemplary configurations for couplers, fittings, ports and adapters may include commercially available luer locks, luer slip ports, locking ports, threaded connections, interlocking connection or generally other common medical device fitting known in the art.

Referring now to the drawings, wherein like reference numerals designate identical or corresponding parts throughout the several views, embodiments of the present disclosure are described as follows.

Figure 2:
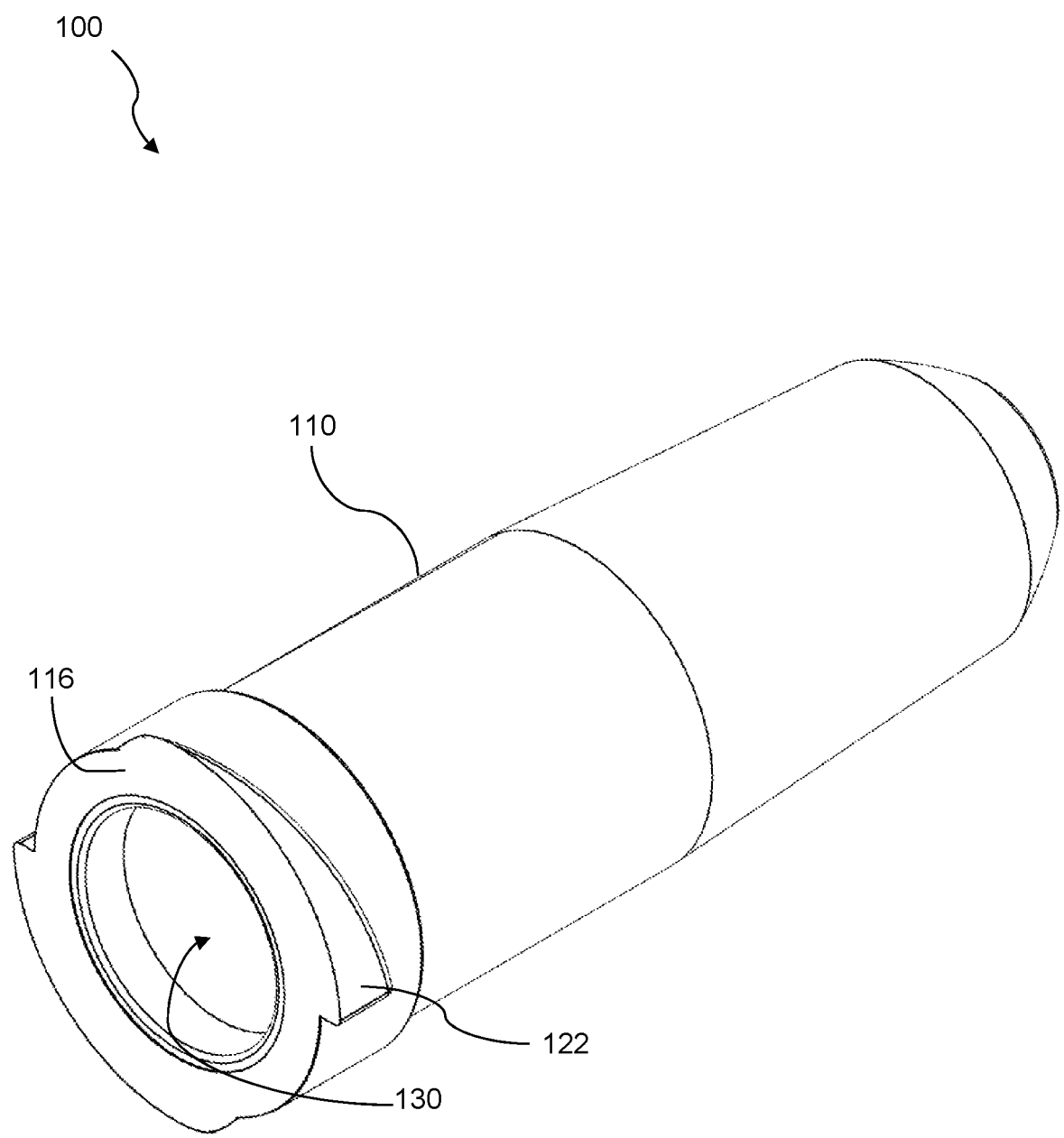
FIG. 2 illustrates a perspective view of the disinfection cap of FIG. 1.

As depicted in FIGS. 1 and 2, a first aspect of the present disclosure relates to a disinfection cap 100 including a housing 110, the housing 110 having an upper portion 110A and a lower portion 110B. In one or more embodiments, the lower portion 110B is substantially cylindrical having a cylindrical housing 112. In one or more alternate embodiments, the lower portion 110B may have a tapered lower portion. The upper portion 110A of the housing has an inwardly tapered sidewall. In further embodiments, the upper portion 110A and lower portion 110B have a substantially cylindrical sidewall. In one or more embodiments, an inner surface 126 of the lower portion 110B of the housing 110 defines a cavity 130 having open bottom 116 for receiving a hub of a needleless connector or more specifically a luer connector. In one embodiment, upper portion 110A is integrally formed with the lower portion 110B while further embodiments are non-removably or removably assembled with a threaded connection, press-fit connection, adhesive connection or a combination thereof.

In one or more embodiments, the cavity 130 can be configured to facilitate a loose fit between the cavity 130 and the hub of the luer connector, wherein the disinfection cap 100 is secured by at least one thread 122 or set of tabs included on the outer surface of the cylindrical housing 112. The at least one thread 122 disposed on the outer surface of the cylindrical housing 112 is sized and have a thread pattern that will engage with a standard ISO-2 type of fitting. The loose fit allows for fluid to flow around the hub of the luer connector. In further embodiments, the cavity 130 can be configured in a Luer Slip fitting to facilitate an interference fit between the cavity 130 and the hub of the luer connector.

In some embodiments, the interference fit can be configured to be sufficiently strong enough to not require a threaded connection (for example, the at least one thread 122) in removably securing the cavity 130 to the luer connector.

In one or more embodiments, when the hub of the luer connector is received within the inner surface 126 of the cavity 130, the hub is secured within the cavity 130 of the disinfection cap 100 by interlocking at least a portion of the at least one thread 122 with a mating feature on the hub of the luer connector. In one or more embodiments, the at least one thread 122 can include an inclined thread pattern. In one or more embodiments, the at least one thread 122 can include a helical-shaped thread pattern. Such connectors are generally and commonly used as catheter and other fluid-tight protective connectors in needleless connectors and more generally in medical applications. In some embodiments, the disinfectant cap 100 provides a protective cover for a luer connector when engaged with the connector when threads from the luer connector engage and form a releasable connection with at least one thread 122 of disinfection cap 100.

Figure 3:
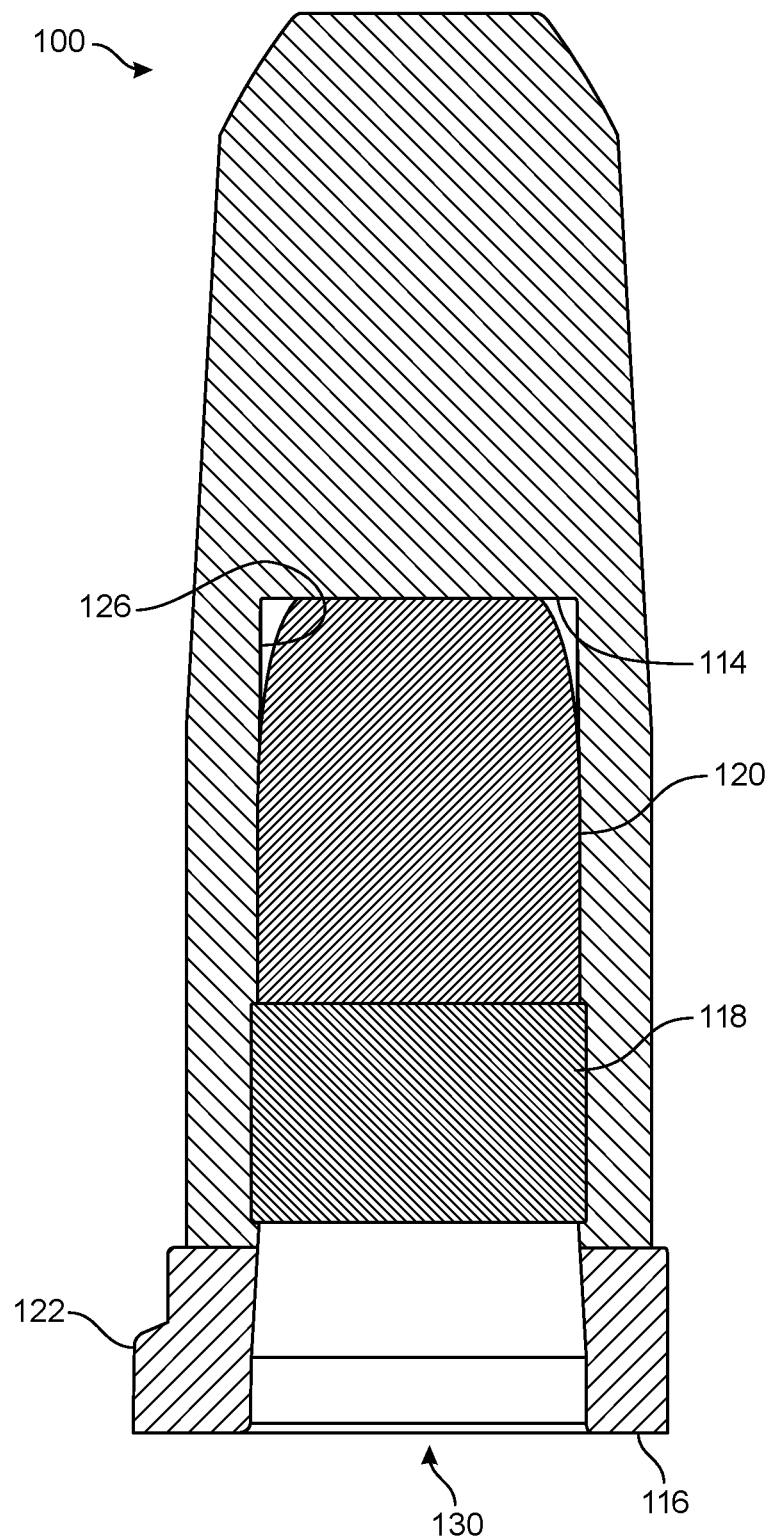
FIG. 3 illustrates a cross sectional view of the disinfection cap along the axis X-X' of the disinfection cap of FIG. 1.

FIG. 3 depicts a cross-sectional view of the disinfection cap 100 along an X-X' plane as shown in FIG. 1. As depicted in FIG. 2, cavity 130 of the housing 110 extends a length of the total length of the housing 110 from the open bottom 116 to a top wall 114, the cavity 130 having a substantially cylindrical shape. Disposed within the cavity is an open cell foam structure 120 for absorbing and retaining disinfectant. The open cell foam structure is impregnated with disinfectant in a pre-activated state. The open cell foam structure 120 can be disposed or abutted against the top wall 114. The open cell foam structure 120 is compressible in both horizontal and vertical directions primarily due to longitudinal advancement of a needleless connector or luer connector against the open cell foam structure 120. In one or more embodiments, the open cell foam structure 120 is sized to create an interference fit with the inner surface 126 of the cavity 130, wherein a diameter of the open cell foam structure 120 is greater than a diameter of the cavity 130. In the preferred embodiment, the open cell foam structure 120 is sized to loosely fit within the cavity, wherein the diameter of the open cell foam structure 120 is smaller than the diameter of the cavity 130. The open cell foam structure 120 allows for fluid to be excreted as the open cell foam structure 120 is compressed.

Figure 4:
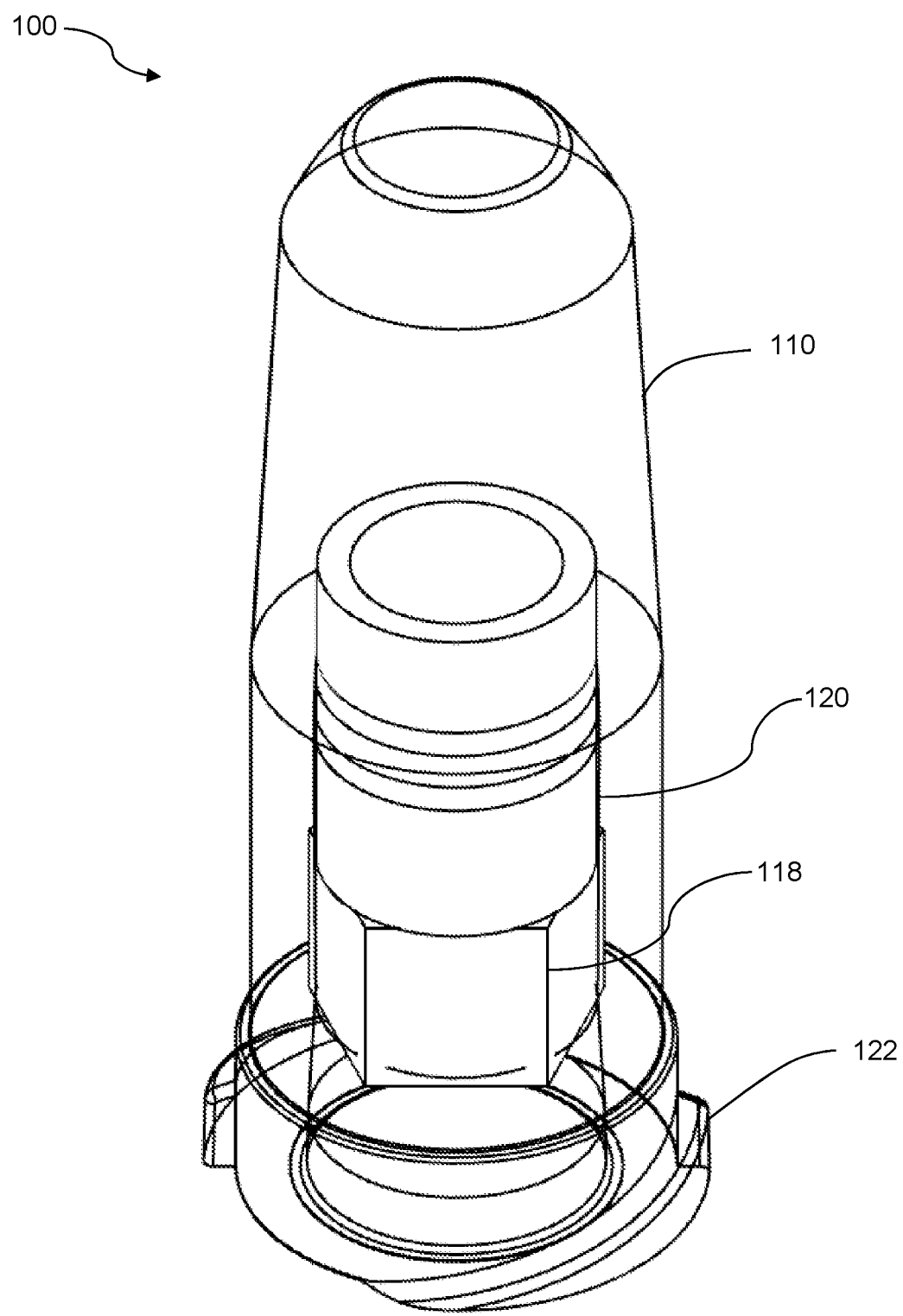
FIG. 4 illustrates a translucent perspective view of the disinfection cap of FIG. 1.
Figure 5A:
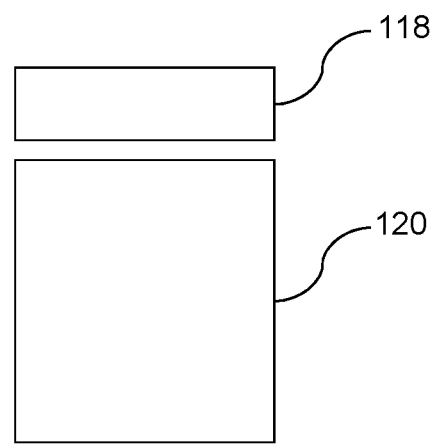
FIGS. 5A and 5B illustrate side views of an open cell foam structure and a closed cell foam structure of the disinfection cap of FIG. 1.
Figure 5B:
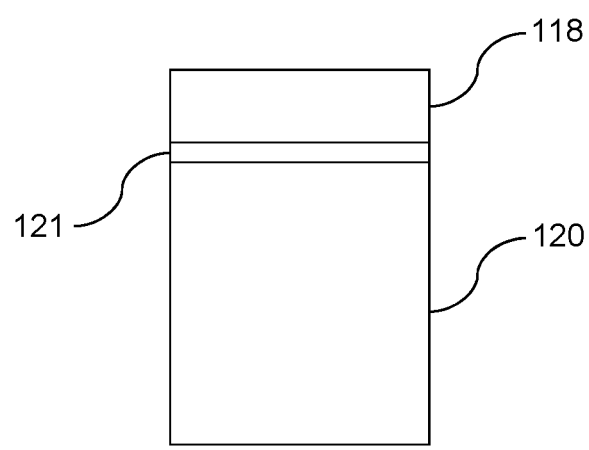

As shown in FIGS. 3 and 4, disposed proximally to the open cell foam structure 120 is a closed cell foam structure 118. The closed cell foam structure 118 resists the absorption of fluids, and is configured to prevent disinfectant ingress into a fluid path of the hub of the luer connector. As shown in FIG. 5A, in one or more embodiments, the open cell foam structure 120 and the closed cell foam structure 118 are two separate single body structures in which the open cell foam structure 120 is disposed on top of the closed cell foam structure 118. As shown in FIG. 5B, in one or more embodiments, the open cell foam structure 120 and the closed cell foam structure 118 are adhered together in a single body with the use of an adhesive layer 121. In one or more embodiments, the open cell foam structure 120 and the closed cell foam structure 118 are of a single cell foam structure having a closed cell foam portion and an open cell foam portion, the open cell foam portion disposed against the top wall 114. In one or more embodiments, the open cell foam structure 120 is independent from the closed cell foam structure 118, the open cell foam structure being first disposed within the cavity 130, against the top wall 114, and the closed cell foam structure 118 being disposed against the open cell foam structure 120. Advancement of a needleless connector or a luer connector into the cavity 130 in a longitudinal connection causes compression of at least the open cell foam structure 120, and in some embodiments the closed cell foam structure 118, against the top wall 114.

In one or more embodiments, the closed cell foam structure 118 can be composed of polyethylene or polyurethane sponge. In one or more embodiments, the adhesive can be a bonding layer of EVA.

The closed cell foam structure 118 is configured to be immobilized within the cavity 130 in a pre-activated state. In some embodiments, the closed cell foam structure 118 creates an interference fit with the inner surface 126 of the cavity 130. The closed cell foam structure 118 has a non-circular cross-sectional shape. As exemplified in the following embodiments, the non-circular cross-sectional shape is configured to create an interference fit with the inner surface 126 of the cavity 130 while still permitting fluid to flow from the open cell foam structure 120 disposed between the top wall 114 and the closed cell foam structure 118 upon compression of the open cell foam structure 120.

Figure 6A:
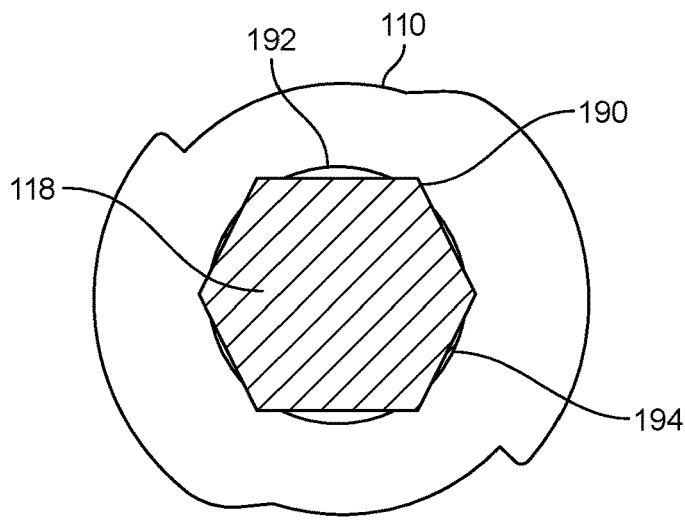
FIGS. 6A through 6E illustrates bottom views of embodiments of the disinfection cap of FIG. 1.
Figure 6B:
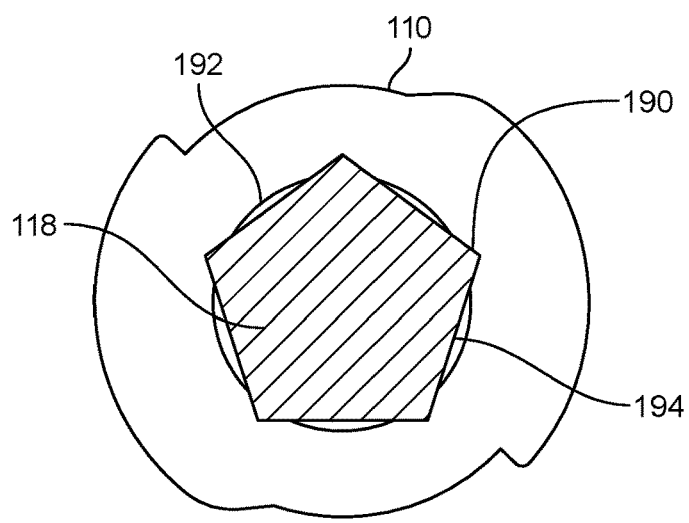
Figure 6C:
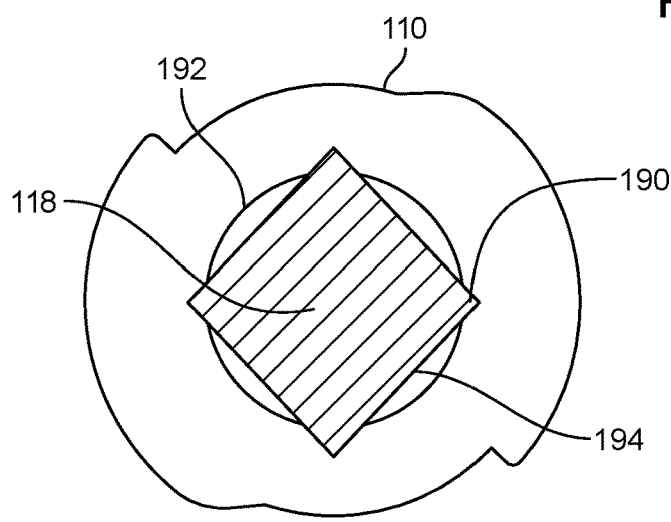

Referring to FIGS. 6A through 6E, embodiments of cross-sectional shapes are illustrated. As illustrated in FIGS. 6A, 6B and 6C, in one or more embodiments, the closed cell foam structure 118 has a polygonal shape, such as a pentagon, a hexagon or a rectangle. In such embodiments, one of a multitude of corners 190 of the polygon shape engages the inner surface 126 of the housing 110 in an interference fit, wherein the distance between one or more of the one of a multitude of corners 190 of the polygon shape are configured to be sized greater than the diameter of the cavity 130. A gap 192 is formed between one of a multitude of flat portions 194 and the inner surface 126 of the housing 110. The one or more gaps 192 are configured to permit fluid to flow between the one of a multitude of flat portions 194 and the inner surface 126 of the housing 110. Upon compression of the open cell foam structure 120 and compression of the closed cell foam structure 118 due to longitudinal advancement of the luer connector 170, disinfectant is excreted from the open cell foam structure 120 and passes through the gap 192, thereby disinfecting the hub 174 and the periphery of the luer connector 170. The closed cell foam structure 118 fluidly seals the lumen 172 of the luer connector 170. The gap 192 creates a fluid pathway for disinfectant to flow through upon compression of the open cell foam structure.

Figure 6D:
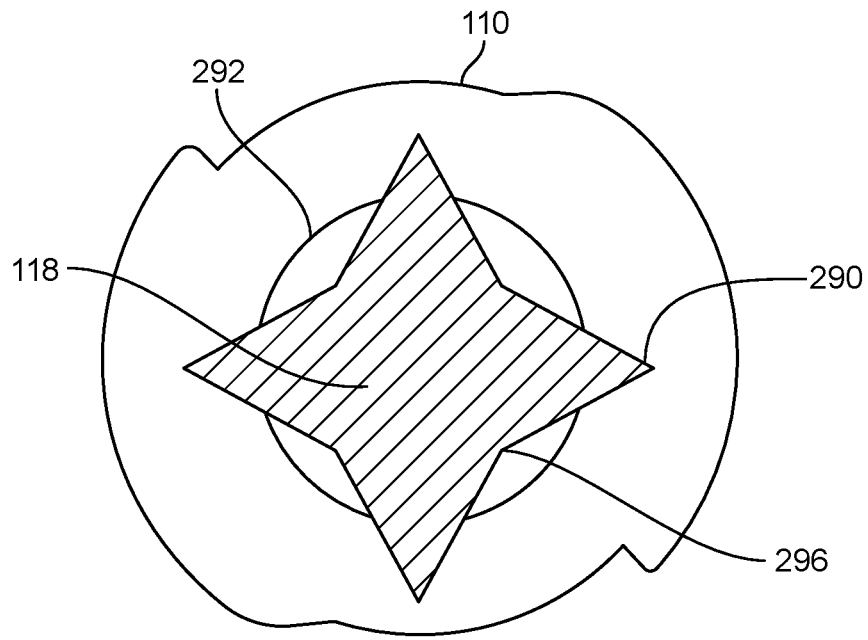
Figure 6E:
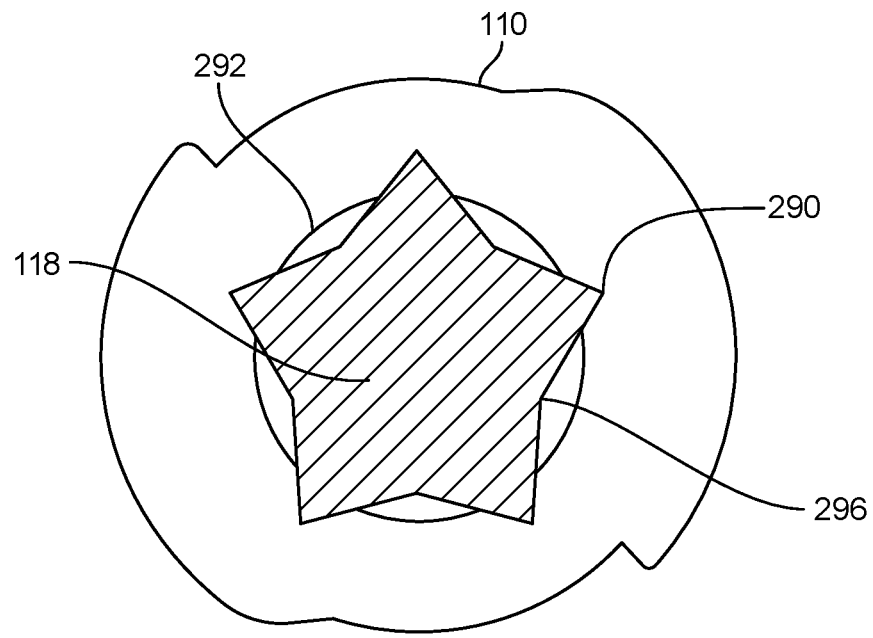

Referring to FIGS. 6D and 6E, in one or more embodiments, the closed cell foam structure 118 has a star shape, such as a four-point star or a five-point star. One of a multitude of points 290 engages the inner surface 126 of the cavity 130 in an interference fit, wherein the distance between one or more of the one of a multitude of points 290 are configured to be sized greater than the diameter of the cavity 130. A gap 292 is formed between one of a multitude of flat portions 294 and the inner surface 126 of the housing 110. The one or more gaps 292 are configured to permit fluid to flow between the one of a multitude of flat portions 294 and the inner surface 126 of the housing 110. The star shape further includes a multitude of inner points 296, creating a larger gap 292 than embodiments having a flat portion 164.

Figure 7:
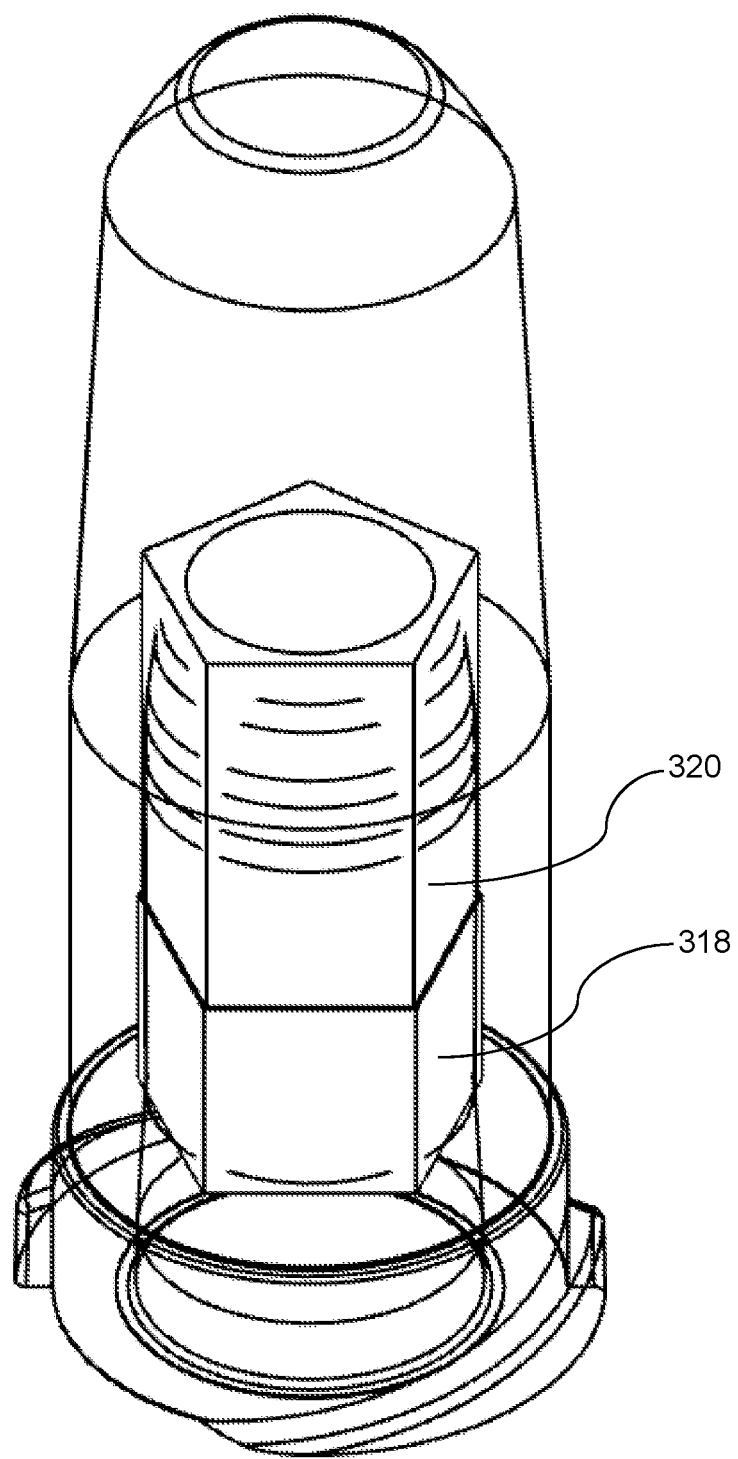
FIG. 7 illustrates a front view of a second embodiment of an exemplary disinfection cap.

In one or more embodiments, the closed cell foam structure is of an oval shape. Referring to FIG. 7, in one or more embodiments, as the closed cell foam structure 318 and the open cell foam structure 320 have the same shape. In one or more embodiments, the closed cell foam structure 318 and the open cell foam structure 320 have a polygonal shape, such as a pentagon, hexagon or rectangle, or a star shape, such as a 4-point star or a 5-point star.

Figure 8:
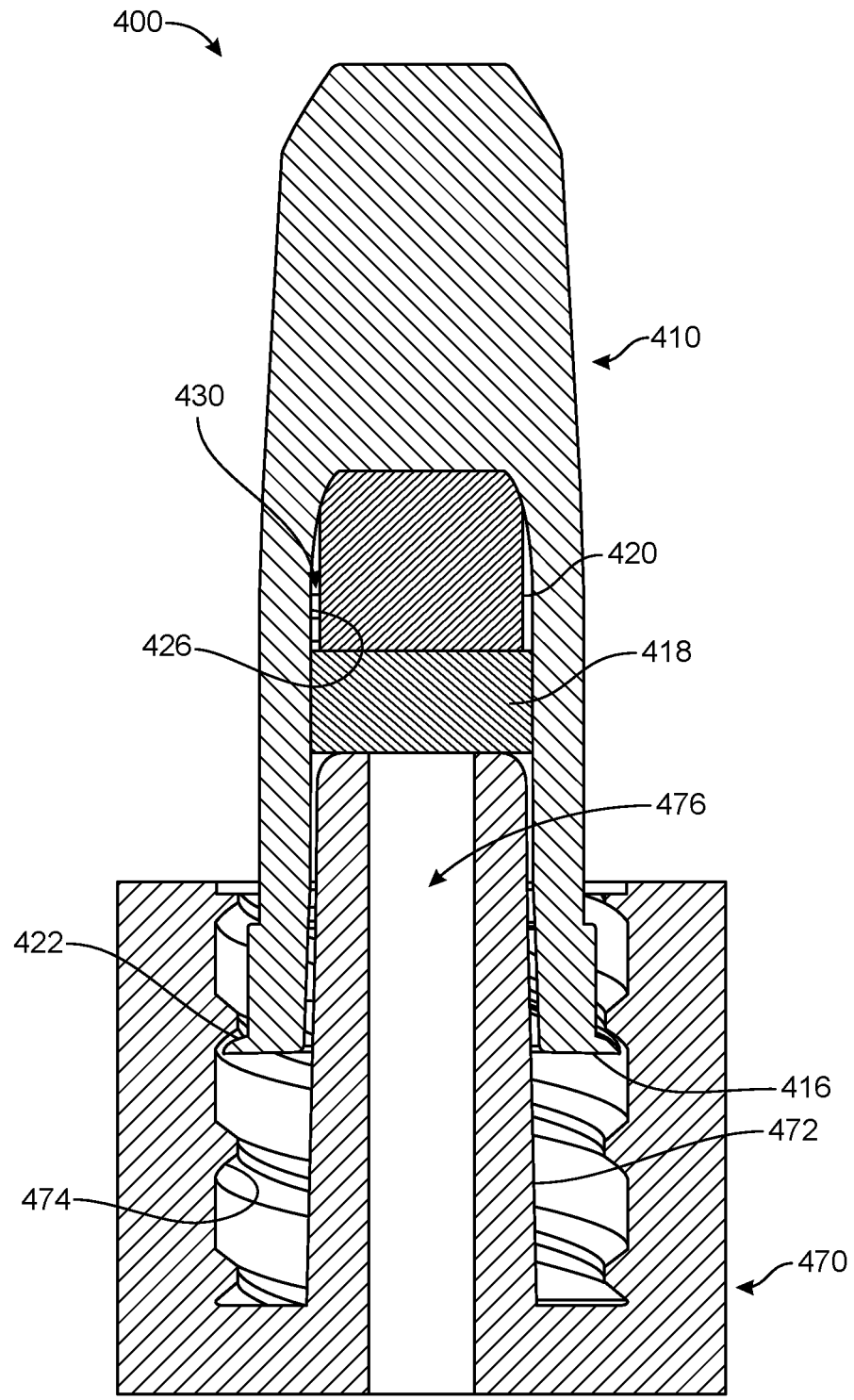
FIG. 8 illustrates a cross-sectional view of a third embodiment of an exemplary disinfection cap.

Referring to FIG. 8, in one or more embodiments, a disinfection cap 400 includes a housing 410 having an inner surface 426 defining a cavity 430 having an open bottom 416 for receiving a hub 472 of a luer connector 470. In one or more embodiments, the cavity 430 can be configured to facilitate a loose fit between the cavity 430 and the hub 472 of the luer connector 470, wherein the disinfection cap 400 is secured by an at least one thread 422 or set of tabs included on the outer surface of the housing. The at least one thread 422 disposed on the outer surface of the cylindrical housing is sized and have a thread pattern that will engage with a standard ISO-2 type of fitting of the luer connector 470. The loose fit allows for fluid to flow around the hub 472 of the luer connector 470. In further embodiments, the cavity 430 can be configured in a Luer Slip fitting to facilitate an interference fit between the cavity 430 and the hub 472 of the luer connector 470. The interference fit can be configured to be sufficiently strong enough to not require a threaded connection or the at least one thread 422 removably securing the cavity 430 to the luer connector 470.

In one or more embodiments, when the hub 472 of the luer connector 470 is received within the inner surface 426 of the cavity 430, the hub 472 is secured within the cavity 430 of the disinfection cap 400 by interlocking at least a portion of the at least one thread 422 with a mating feature or threads 474 on the hub of the luer connector 470. In one or more embodiments, the at least one thread 422 can include an inclined thread pattern. In one or more embodiments, the at least one thread 422 can include a helical-shaped thread pattern. Such connectors are generally and commonly used as catheter and other fluid-tight protective connectors in medical applications. In some embodiments, the disinfectant cap 400 provides a protective cover for a luer connector when engaged with the connector when threads 474 of the luer connector 470 engage and form a releasable connection with at least one thread 422 of disinfection cap 400.

Upon compression of an open cell foam structure 420 disposed within the cavity 430 and compression of a closed cell foam structure 418 disposed proximally to the open cell foam structure 420, disinfectant is excreted from the open cell foam structure 420 and passes through a gap, disinfecting the hub 472 and the periphery of the luer connector 470. The closed cell foam structure 418 fluidly seals the lumen 476 of the luer connector 470. The gap creates a fluid pathway for disinfectant to flow through upon compression of the open cell foam structure 420.

Having the same shape for the open cell foam structure and closed cell foam structure is beneficial in manufacturing of the disinfectant cap. In manufacturing, sheets of open cell foam bonded together with closed cell foam can be cut to the appropriate shape in a single manufacturing step, instead of bonding pre-cut open cell foam structures to closed cell foam structures individually. A method of manufacturing comprises bonding sheets of closed cell foam to open cell foam into a bonded open cell foam structure and closed cell foam structure, cutting the bonded open cell foam structure and closed cell foam structure into a shape and inserting the bonded open cell foam structure and closed cell foam structure into a cavity of a molded housing. In one or more embodiments, the sheets of closed cell foam and the sheets of open cell foam are of an industrial size. In one or more embodiments, the shape of the bonded open cell foam structure and closed cell foam structure are of a polygonal shape, a star shape or oval shape.

In one or more embodiments, the method further includes impregnating the open cell foam structure with disinfectant before inserting the bonded open cell foam structure and closed cell foam structure. In one or more embodiments, the method further includes impregnating the open cell foam structure with a disinfectant through a gap formed between a flat portion of the closed cell foam structure and an inner surface of the cavity of the housing.

The method of manufacturing further includes placing a peelable seal on an open end of the housing to seal the cavity and the disinfectant within.

The disinfection cap 100 can achieve disinfection when used on needleless connectors or more specifically luer connectors by integrating disinfectant in the cavity 130 of the disinfection cap 100. The disinfectant can be directly included in the cavity 130. The disinfection cap 100 is configured to be compatible in interacting with various disinfectant or antimicrobial agents or fluid. In one or more embodiments, the disinfectant or antimicrobial agent or fluid includes variations of alcohol or chlorhexidine. In one or more embodiments, the disinfectant or antimicrobial agent or fluid includes variations of alcohol or chlorhexidine.

In one or more embodiments, the disinfectant is selected from the group consisting essentially of isopropyl alcohol, ethanol, 2-propanol, butanol, methylparaben, ethylparaben, propylparaben, propyl gallate, butylated hydroxyanisole (BHA), butylated hydroxytoluene, t-butyl-hydroquinone, chloroxylenol, chlorohexidine, chlorhexidine diacetate, chlorhexidine gluconate, povidone iodine, alcohol, dichlorobenzyl alcohol, dehydroacetic acid, hexetidine, triclosan, hydrogen peroxide, colloidal silver, benzethonium chloride, benzalkonium chloride, octenidine, antibiotic, and mixtures thereof. In a specific embodiment, the disinfectant or antimicrobial agent comprises at least one of chlorhexidine gluconate and chlorhexidine diacetate. In one or more embodiments, the disinfectant or antimicrobial agent is a fluid or a gel.

In one or more embodiments, the disinfection cap 100 can include a removable peelable seal covering the opening to the cavity 130. In one or more embodiments, the peelable seal comprises an aluminum or multi-layer polymer film peel back top. In a specific embodiment, the peelable is heat-sealed or induction sealed to the open end of the disinfection cap 100. In one or more embodiments, the peelable seal comprises a moisture barrier. In some embodiments, the peelable seal is thin enough to be punctured by the luer connector such that the luer connector is advanceable within the cavity 130 without having to first remove the peelable seal.

The disinfection cap 100 is made from any of a number of types of plastic materials such as polycarbonate, polypropylene, polyethylene, polyethylene terephthalate, polylactide, acrylonitrile butadiene styrene or any other moldable plastic material used in medical devices. In one or more embodiments, the disinfection cap 100 comprises a polypropylene or polyethylene material.

In one or more embodiments, the connector of the medical device may be selected from the group consisting essentially of needle-free connectors, catheter luer connectors, stopcocks, and hemodialysis connectors on primary IV gravity sets, secondary IV gravity sets, extension sets, and infusion or syringe pump sets. In some embodiments, the disinfection cap can be connected with any of a variety of different needleless injection sites. In one or more embodiments, after the disinfection cap has been coupled with connector, it is unnecessary to disinfect (e.g., treat with an alcohol swab) the connector prior to each reconnection of the connector with another connector, as the connector will be kept in an uncontaminated state while coupled with the disinfection cap. Use of the disinfection cap 100 replaces the standard swabbing protocol for cleaning connectors.

Yet another aspect of the present disclosure pertains to a method of disinfecting a medical connector. The method comprises connecting the disinfection cap 100 of one or more embodiments to a medical connector, wherein connecting includes engaging the threads of the medical connector onto the threads on the outer surface of the sidewall of the housing 110 of the disinfection cap upon insertion of the medical connector into the disinfection cap 100 such that the medical connector contacts the blockage feature. In one or more embodiments, the blockage feature is a closed cell foam structure 118.

It is contemplated that the disinfection cap 100 disclosed herein and shown in the figures may also be utilized with luer connectors, including female and male luer connectors, wherein the blockage feature can be used to block the lumen of open luers to facilitate the mitigation of such disinfectant ingress into connectors, thereby reducing risk of the disinfectant entering the blood stream. It is therefore contemplated that the disinfection cap 100 disclosed herein and shown in the figures may be utilized with male and female luer connectors.

While the present disclosure has been shown and described with reference to certain exemplary embodiments thereof, it will be understood by those skilled in the art that various changes in form and details may be made therein without departing from the spirit and scope of the embodiments of the present disclosure. Also, the housing of the disinfection cap can be single shot molded, or made by other suitable process. Furthermore, any of the features or elements of any exemplary implementations of the embodiments of the present disclosure as described above and illustrated in the drawing figures can be implemented individually or in any combination(s) as would be readily appreciated by skilled artisans without departing from the spirit and scope of the embodiments of the present disclosure.

In addition, the included drawing figures further describe non-limiting examples of implementations of certain exemplary embodiments of the present disclosure and aid in the description of technology associated therewith. Any specific or relative dimensions or measurements provided in the drawings other as noted above are exemplary and not intended to be limiting.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has provided a description with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A disinfection cap having a housing comprising:
   a top wall and a cylindrical sidewall having an inner surface defining a cavity, and an outer surface,
   an open bottom formed by the cylindrical sidewall with an opening to the cavity within said housing for receiving a hub of a luer connector;
   an open cell foam structure disposed within the cavity, the open cell foam structure abutting a top wall of the cavity, the open cell foam structure being impregnated with disinfectant fluid in a pre-activated state; and
   a closed cell foam structure disposed against the open cell foam structure, the closed cell foam structure being configured as a blockage feature for fluidly blocking the hub of the luer connector, wherein when the hub of said luer connector is received within said inner surface of said cavity wherein the open cell foam structure is bonded to the closed cell foam structure, the closed cell foam structure and the open cell foam structure both have the same non-circular cross-sectional shape said non-circular cross-sectional shape is configured to create an interference fit with the inner surface of the cavity while still permitting fluid to flow from the open cell foam structure disposed between the top wall and the closed cell foam structure upon compression of the open cell foam structure.

2. The disinfection cap of claim 1, wherein insertion of the luer connector causes compression of the open cell foam structure, thereby releasing fluid.

3. The disinfection cap of claim 1, wherein the closed cell foam structure has a polygonal shape.

4. The disinfection cap of claim 3, wherein the closed cell foam structure has one of a multitude of corners which engage the inner surface of the housing in an interference fit.

5. The disinfection cap of claim 4, wherein a gap is formed between one of a multitude of flat portions and the inner surface of the housing, the gap creating a pathway for disinfectant to flow through upon compression of the open cell foam structure.

6. The disinfection cap of claim 5, wherein said hub is secured within said inner surface of said cavity by interlocking at least a portion of at least one thread with a mating feature on said hub of said luer connector.

7. The disinfection cap of claim 3, wherein the closed cell foam structure has a hexagonal shape.

8. The disinfection cap of claim 3, wherein the closed cell foam structure has a pentagonal shape.

9. The disinfection cap of claim 3, wherein the closed cell foam structure has a four-point star shape.

10. The disinfection cap of claim 3, wherein the closed cell foam structure has a five point star shape.

11. The disinfection cap of claim 1, wherein the closed cell foam structure has a star shape.

12. The disinfection cap of claim 11, wherein the closed cell foam structure has one of a multitude of points which engage the inner surface of the housing in an interference fit.

13. The disinfection cap of claim 12, wherein a gap is formed between one of a multitude of inner points and the inner surface of the housing, the gap creating a pathway for disinfectant to flow through upon compression of the open cell foam structure.

14. The disinfection cap of claim 1, further including an at least one thread on said outer surface of the housing, said at least one thread being sufficient to interlock with a mating feature of the luer connector.

15. The disinfection cap of claim 1, wherein a removable peelable seal covers an opening to the cavity.

16. The disinfection cap of claim 1, wherein the open cell foam structure has a polygonal shape.

17. The disinfection cap of claim 1, wherein the open cell foam structure has a star shape.

18. A method of manufacturing of the disinfection cap of claim 1, comprising:
bonding sheets of the closed cell foam to the open cell foam into a bonded open cell foam structure and closed cell foam structure;
cutting the bonded open cell foam structure and closed cell foam structure into a shape; and,
inserting the bonded open cell foam structure and closed cell foam structure into the cavity of the housing of the disinfection cap.

19. The method of manufacturing of claim 18 further comprising:
impregnating the bonded open cell foam structure with disinfectant before inserting the bonded open cell foam structure and closed cell foam structure.

20. The method of manufacturing of claim 18 further comprising:
impregnating the bonded open cell foam structure with a disinfectant through a gap formed between a flat portion of the closed cell foam structure and an inner surface of the cavity of the housing.

21. The method of manufacturing of claim 18 further comprising:
placing a peelable seal on an open end of the housing to seal the cavity and the disinfectant within.

* * * * *